(12) United States Patent
Roehrig

(10) Patent No.: US 11,058,789 B2
(45) Date of Patent: Jul. 13, 2021

(54) SCENT DISPENSER DEVICE AND A HEAD MOUNTING DEVICE WITH THE SCENT DISPENSER DEVICE

(71) Applicant: Joshua Roehrig, Greenock, PA (US)

(72) Inventor: Joshua Roehrig, Greenock, PA (US)

( * ) Notice: Subject to any disclaimer, the term of this patent is extended or adjusted under 35 U.S.C. 154(b) by 144 days.

(21) Appl. No.: 16/510,883

(22) Filed: Jul. 13, 2019

(65) Prior Publication Data
US 2020/0179554 A1 Jun. 11, 2020

Related U.S. Application Data

(60) Provisional application No. 62/698,288, filed on Jul. 16, 2018.

(51) Int. Cl.
*A61L 9/12* (2006.01)
*A63J 25/00* (2009.01)
*A42B 7/00* (2006.01)
*A63J 5/00* (2006.01)

(52) U.S. Cl.
CPC ............... *A61L 9/125* (2013.01); *A42B 7/00* (2013.01); *A63J 25/00* (2013.01); *A63J 2005/008* (2013.01)

(58) Field of Classification Search
CPC ..... A61L 9/125; A63J 25/00; A63J 2005/008; A63F 13/28; A42B 7/00
See application file for complete search history.

(56) References Cited

U.S. PATENT DOCUMENTS

| 4,629,604 | A | | 12/1986 | Spector | |
|---|---|---|---|---|---|
| 5,565,148 | A | * | 10/1996 | Pendergrass, Jr. | ...... A61L 9/122 261/30 |
| 5,734,590 | A | * | 3/1998 | Tebbe | ...... A61L 9/125 700/94 |
| 5,949,522 | A | * | 9/1999 | Manne | ...... A63J 5/00 352/85 |
| 6,136,277 | A | * | 10/2000 | Nardini | ...... A61L 9/122 360/132 |
| 6,169,595 | B1 | | 1/2001 | Manne | |
| 7,154,579 | B2 | * | 12/2006 | Selander | ...... A61L 9/125 352/85 |
| 8,295,529 | B2 | | 10/2012 | Peterson | |
| 2003/0026728 | A1 | * | 2/2003 | Avram | ...... A63J 5/00 422/4 |
| 2017/0266676 | A1 | | 9/2017 | Fateh | |
| 2018/0147484 | A1 | * | 5/2018 | Osawa | ...... A61L 9/122 |

FOREIGN PATENT DOCUMENTS

FR 2553666 A1 * 4/1985 ............. A61L 9/125

* cited by examiner

*Primary Examiner* — Ryan A Reis

(57) ABSTRACT

A scent dispenser device and a head mounting device including the scent dispenser device is provided. The scent dispenser device may be used by a subject watching a motion picture in order to enhance the user experience of a motion picture. The scent dispenser device includes a first housing, which in turn includes a tape cartridge and a drive mechanism. The scent dispenser device is positioned close to the nostrils of the subject, and the tape cartridge includes one or more scent zone. The drive mechanism advances the tape cartridge inside the first housing, and the scent from the one or more scent zone is exposed to the nostrils of the subject, in case the drive mechanism is in operation.

6 Claims, 18 Drawing Sheets

SCENT DISPENSER DEVICE AND A HEAD MOUNTING DEVICE WITH THE SCENT DISPENSER DEVICE

CROSS REFERENCE TO RELATED APPLICATIONS

This application claims priority to U.S. Provisional Application 62/698,288 filed on Jul. 16, 2018 entitled "SYSTEM, METHOD, AND SCENT SENSORY DEVICE FOR SEMI-PRESENT EXPERIENCE THROUGH MOTION PICTURES".

BACKGROUND

Field

In general, the subject matter relates to techniques for enhancing the motion picture viewing experience, more particularly, but not exclusively to a scent dispenser device for dispensing one or more fragrance to a viewer of a motion picture.

Discussion of Related Field

Incorporating additional senses to a motion picture, to enhance the user experience and compliment the conventional audio and visuals information has been under research and development for several years now.

Conventional research is focused more on inclusion of odor or scent to a motion picture to enhance viewer experience. Manne in U.S. Pat. No. 6,169,595 teaches a computer-controlled system coupled with an air compressor to deliver scent individually to each viewer through a tube under the nose. Fateh in US published application 2017/0266676 discloses a head-mounted device that includes means for delivering scents to the wearer near the nose, using scented liquid capsules. Petersen in U.S. Pat. No. 8,295,529 discloses a gaming headset that includes ability to deliver olfactory stimulation. Spector in U.S. Pat. No. 4,629,604 teaches a scent cartridge machine that works in conjunction with a video player.

The above prior arts have proposed solutions which can be applied in a cinema hall, or for a group of viewers. Thus, they are not suitable for personal usage, where portability is of prime importance. Further, Fateh proposes a head-mounted device that delivers scents to a viewer. The technique uses liquid capsules to deliver scent. However, there is a limit to the number of liquid scent capsules that may be attached to the head mounted device. This further restricts a viewer experience to two or three choices of fragrances for an entire motion picture of any length. Thus, conventional prior art fails to propose a solution or solve the problem of enhancing the user experience of a motion picture with respect to the sense of smell.

In view of the forgoing, there is a need for an improved technique that can efficiently solve the above problem and enhance the user experience of watching a motion picture.

SUMMARY

Accordingly, a technique to overcome the above problems is needed. To fulfill this need, a scent dispenser device and a head mounting device including the scent dispenser device, which can be used by a subject watching a motion picture in order to enhance the user experience of a motion picture is provided. In an embodiment, a scent dispenser device includes a first housing, which in turn includes a tape cartridge and a drive mechanism. The scent dispenser device is positioned close to the nostrils of the subject, and the tape cartridge includes one or more scent zone. The drive mechanism advances the tape cartridge inside the first housing, and the scent from the one or more scent zone is exposed to the nostrils of the subject, in case the drive mechanism is in operation.

In another embodiment, the tape cartridge further comprises a first film and a second film. The one or more scent zone is sandwiched between the first film and the second film, such that the one or more scent zone is sealed therebetween.

In another embodiment, the outer surface of the first film includes one or more black strip.

In another embodiment, the first housing further comprises a nose piece configured to split the tape cartridge into the first film and the second film, such that the scent from the one or more scent zone is exposed to the nostrils of the subject by the nose piece.

In another embodiment, the nose piece is movably attached to the drive mechanism of the first housing, such that the position of the nose piece with respect to the first housing is adjustable.

In another embodiment, the first housing includes a cartridge spool and a cylindrical protrusion. The tape cartridge is spooled to the cartridge spool and the cylindrical protrusion, which is within the first housing secures the position of the cartridge spool.

In another embodiment, the drive mechanism comprises a first spool gear and a second spool gear positioned such that the first spool gear drives the second spool gear in case the drive mechanism is in operation.

In another embodiment, the scent dispenser device includes an actuator operably coupled to the first spool gear to actuate the drive mechanism.

In another embodiment, the scent dispenser device includes a second housing, which includes an actuator secured in the second housing. Further, the second housing is detachably connected to the first housing, such that the actuator drives the first spool gear in the first housing.

In another embodiment, the second housing includes a photoresistor and a Light Emitting Diode (LED). The photoresistor and the LED are positioned against the tape cartridge in case the first housing is connected to the second housing, such that the light emitted by the LED is reflected of the tape cartridge, and the reflected light is received by the photoresistor.

In another embodiment, the first housing further comprises a slit bridge to maintain tension in the tape cartridge within the first housing. The slit bridge is positioned between the cartridge spool and the first spool gear in the first housing. The outer surface of the tape cartridge is exposed from the first housing at the slit bridge before passing through the drive mechanism.

In another embodiment, the tape cartridge, which is split into first film and the second film, by the nose piece, are spooled at the second spool gear and the first spool gear, respectively. An actuator actuating the first spool gear advances the tape cartridge in the first housing through the nose piece.

In an embodiment, a head mounting device is provided. The head mounting device includes a body frame, a scent dispenser device, and a controller operably connected to the scent dispenser device. The body frame is configured to secure the head mounting device to a subject's head. The scent dispenser device attached to the body frame and is used by a subject watching a motion picture. The scent dispenser device includes a first housing, which in turn includes a tape cartridge and a drive mechanism. The scent dispenser device is positioned close to the nostrils of the subject, and the tape cartridge includes one or more scent zone. The drive mechanism advances the tape cartridge inside the first housing, and the scent from the one or more scent zone is exposed to the nostrils of the subject, in case the drive mechanism is in operation. The controller is communicably connected to the scent dispenser device, which operates the drive mechanism.

In another embodiment, the drive mechanism includes a first spool gear and a second spool gear positioned such that the first spool gear drives the second spool gear in case the drive mechanism is in operation. The head mounting device includes a second housing, where an actuator is secured, and the second housing is detachably connected to the first housing, such that the actuator drives the first spool gear in the first housing. The actuator is operably coupled to the first spool gear to actuate the drive mechanism. The second housing further comprises a photoresistor and a Light Emitting Diode (LED). The photoresistor and the LED are positioned against the tape cartridge when the first housing is connected to the second housing, such that the light emitted by the LED is reflected of the tape cartridge and the reflected light is received by the photoresistor. The controller is configured to detect the change in a reflection measurement of the photoresistor, and modify the operation of the actuator Other objects, features, and advantages of the present invention may become apparent from the following detailed description. It shall be understood that, the detailed description and specific examples, while indicating preferred embodiments of the present invention, are given by way of illustration only and various modifications may naturally be performed without deviating from the scope of the present invention.

BRIEF DESCRIPTION OF THE DRAWINGS

Embodiments are illustrated by way of example and not limited by the Figures of the accompanying drawings, in which like references indicate similar elements and in which.

DETAILED DESCRIPTION

The following detailed description includes references to the accompanying drawings, which form a part of the detailed description. The drawings show illustrations in accordance with example embodiments. These example embodiments are described in enough detail to enable those skilled in the art to practice the present subject matter. However, it will be apparent to one with ordinary skill in the art that the present invention may be practiced without these specific details. In other instances, well-known methods, procedures, components, wiring and circuits have not been described in detail so as not to unnecessarily obscure aspects of the embodiments. The embodiments can be combined, other embodiments can be utilized, or structural, logical modifications can be made without departing from the scope of what is claimed. The following detailed description describes the best mode of the invention and is, therefore, not to be taken as a limiting sense.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated.

The embodiments disclose techniques to enhance the user experience of a viewer watching a motion picture. For example, an embodiment provides a scent dispenser device and a head mounting device including the scent dispenser device to enhance the user experience of a subject watching a motion picture. The scent dispenser device includes a tape cartridge and a drive mechanism. The tape cartridge includes one or more scent zone. The drive mechanism advances the tape cartridge inside a first housing, and the scent from the one or more scent zone is exposed to the nostrils of the subject, in case the drive mechanism is in operation.

Structure of the Scent Dispenser Device 1000

Figure 1:
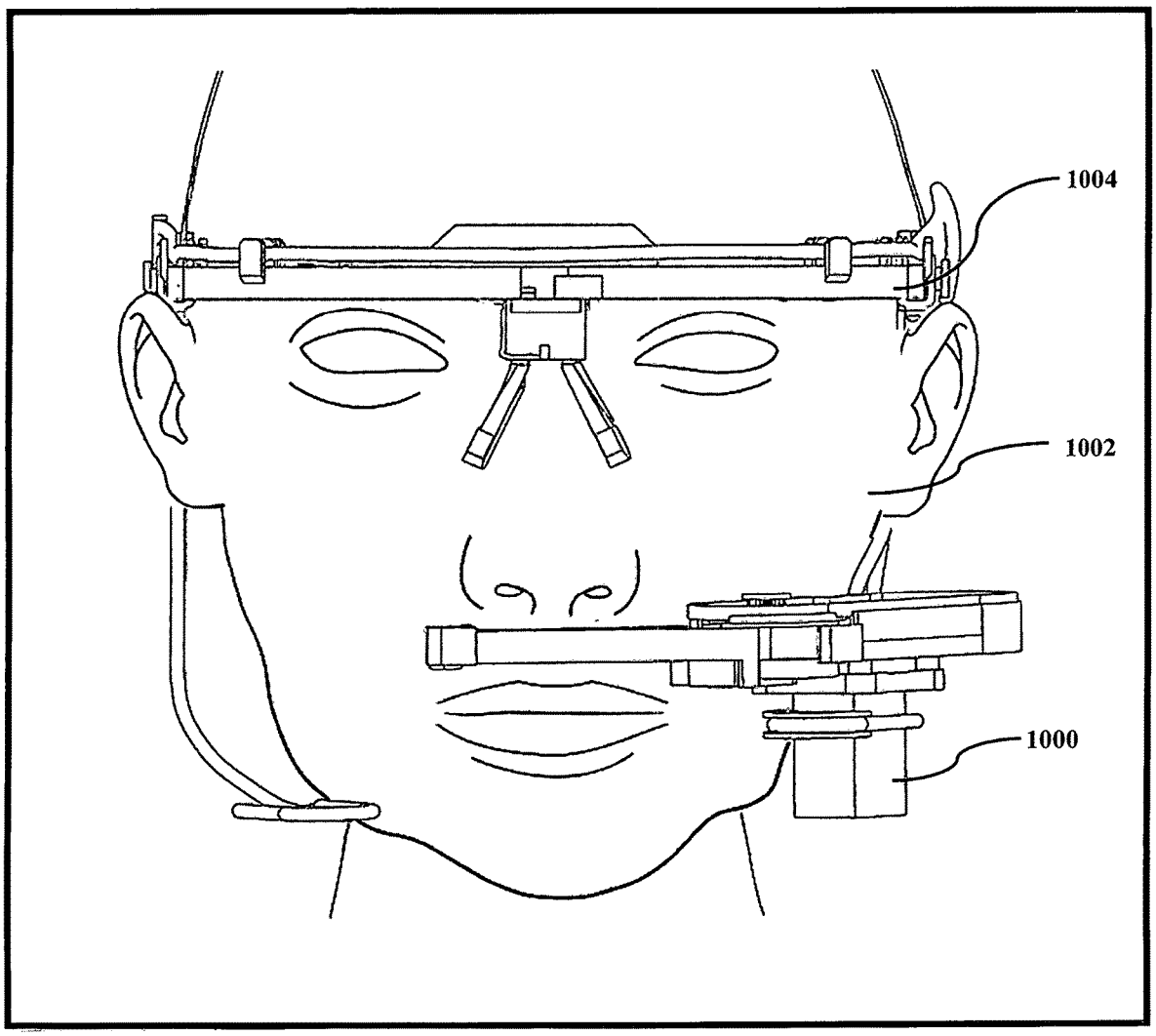
FIG. 1 depicts an exemplary view of a head mounting device 1004 with a scent dispenser device 1000 secured to a subject 1002, in accordance with an embodiment of the invention.

FIG. 1 depicts an exemplary view of a head mounting device 1004 with a scent dispenser device 1000 secured to a subject 1002, in accordance with an embodiment of the invention. The operation of the scent dispenser device 1000 is controlled by a controller 1006 (not shown in the FIGS.). As depicted in the instant figure, the scent dispenser device 1000 is connected to the head mounting device 1004, which is secured to the head of the subject 1002. The scent dispenser device 1000 is positioned close to the nostrils of the subject 1002, such that the exposed scent may be sensed by the subject 1002. In an embodiment, the head mounting device 1004 may include one or more additional modules to enhance the user experience of the subject 1002 watching a motion picture or playing a video game.

Figure 2A:
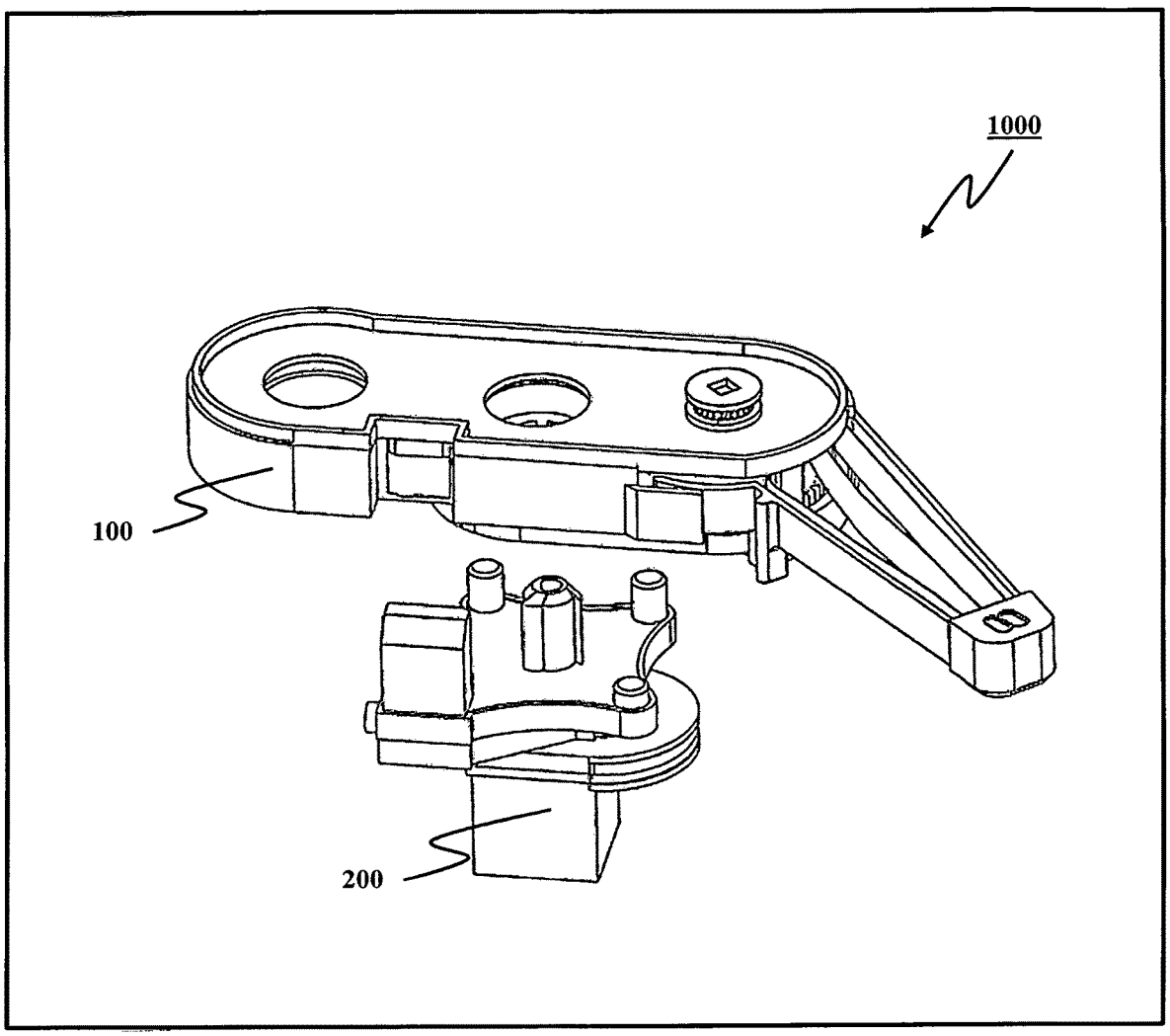
FIGS. 2A-2C depicts exemplary views of a first housing 100 and a second housing 200 of the scent dispenser device 1000 in disengaged position, in accordance with an embodiment of the invention.
Figure 2B:
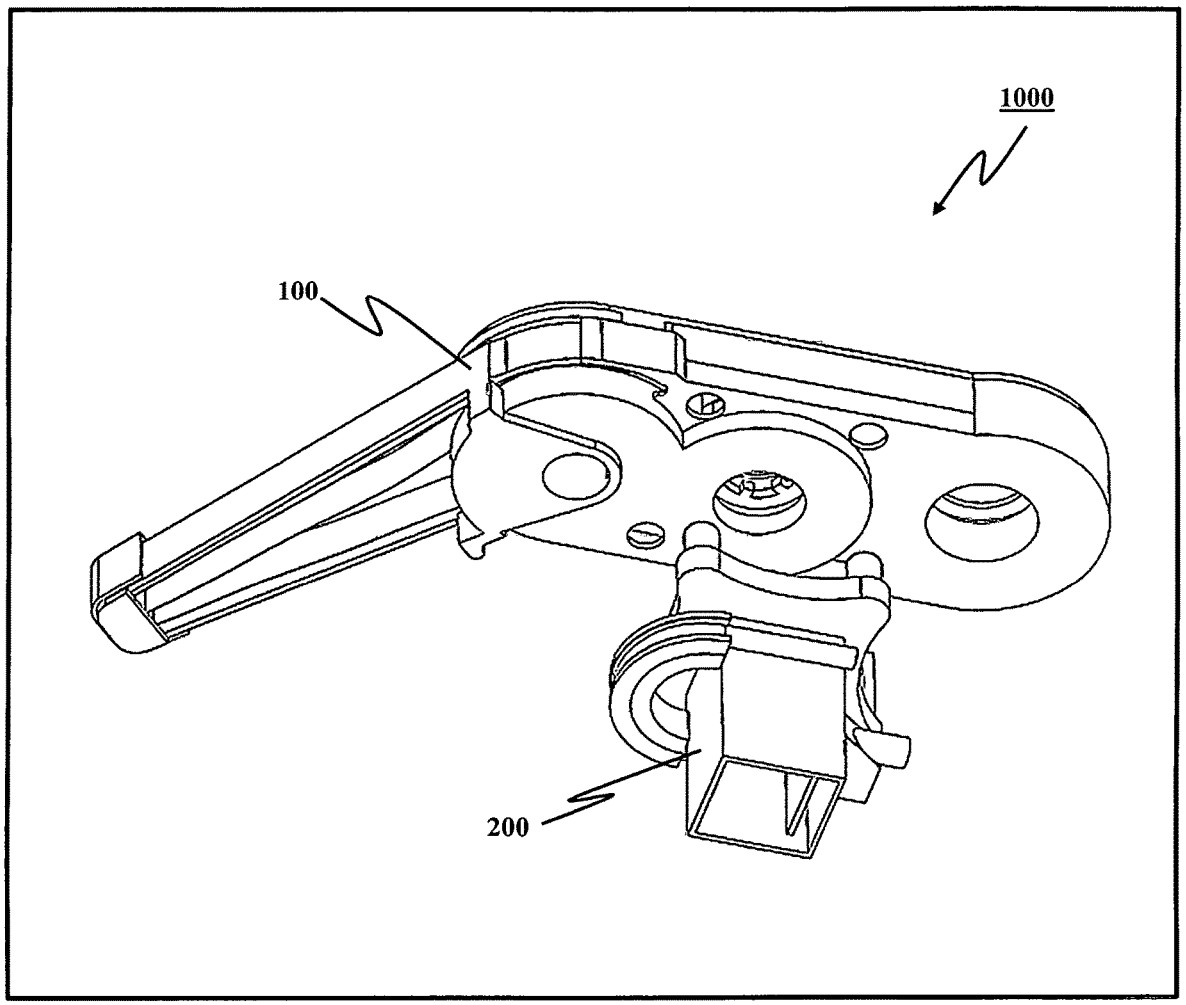
Figure 2C:
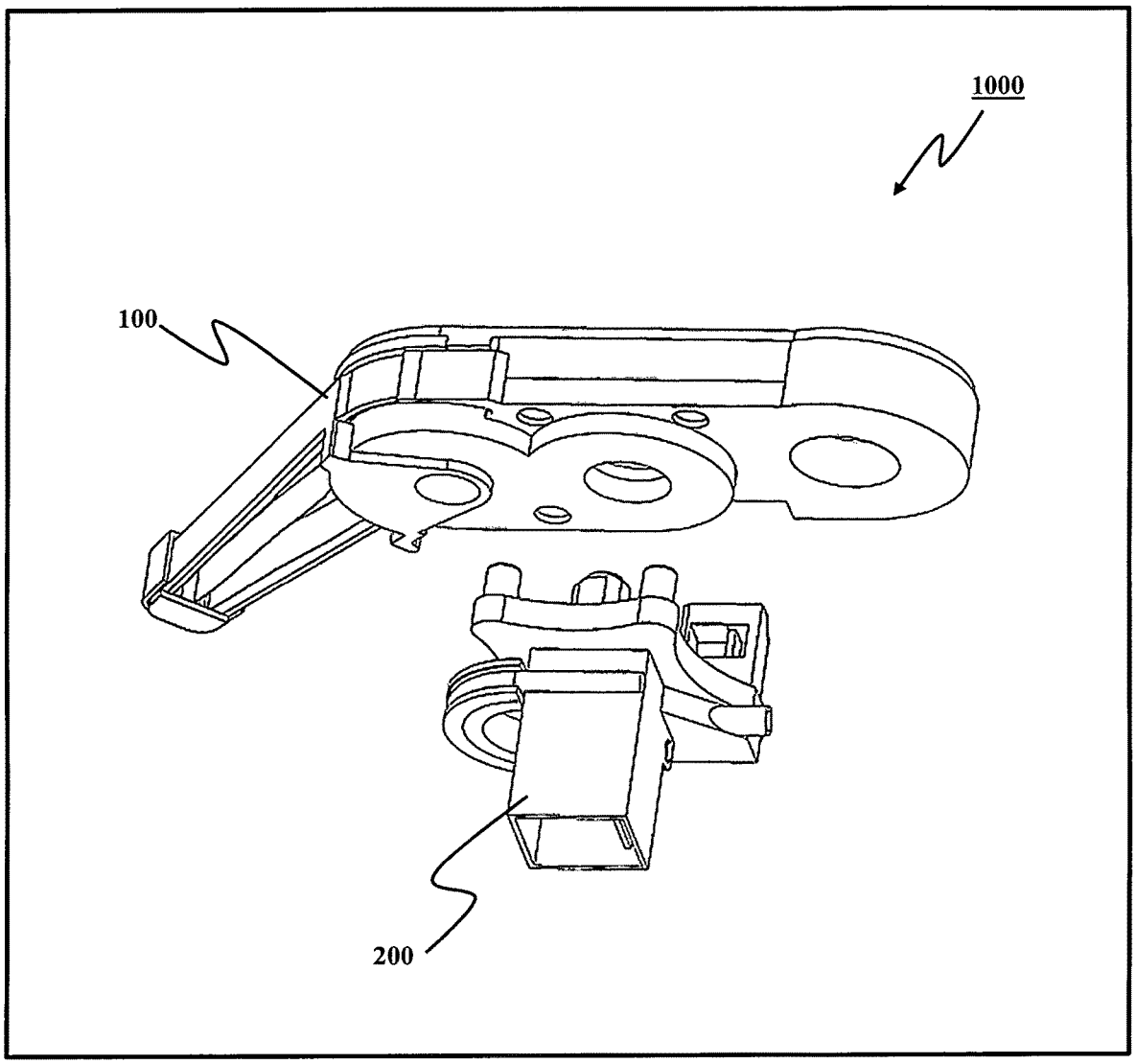

FIGS. 2A-2C depicts exemplary views of a first housing 100 and a second housing 200 of the scent dispenser device 1000 in disengaged position, in accordance with an embodiment of the invention. As depicted in the above figures the scent dispenser device 1000 includes the first housing 100 and the second housing 200. The first housing 100 and the second housing 200 are detachably connected. For example, the figures depict one exemplary way of detachably connecting the first housing 100 and the second housing 200 through one or more protrusion and one or more recess on the bottom surface of the first housing 100 and the top surface of the second housing 200.

Figure 3A:
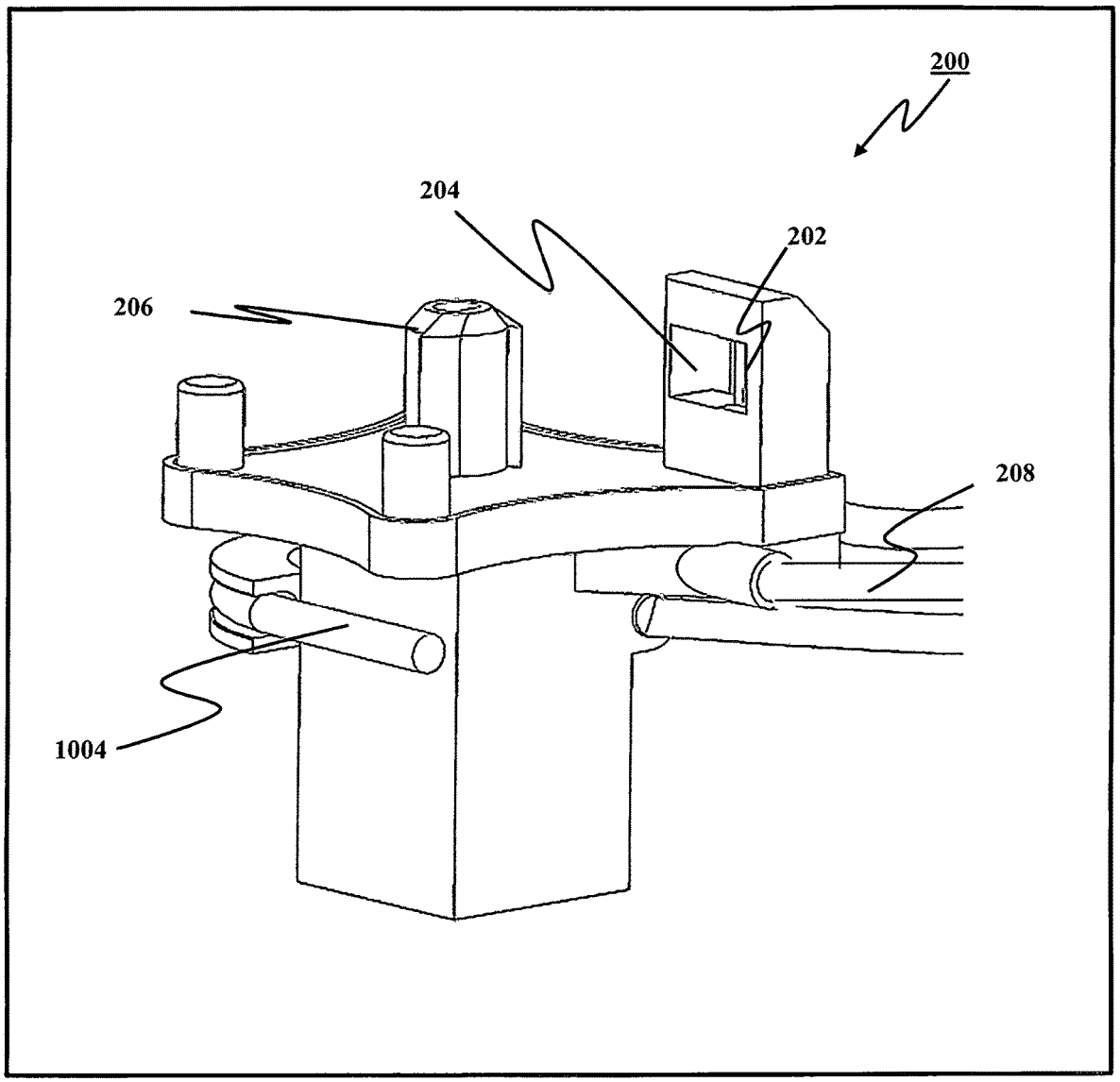
FIGS. 3A & 3B depicts exemplary views of the second housing 200 in accordance with an embodiment of the invention.
Figure 3B:
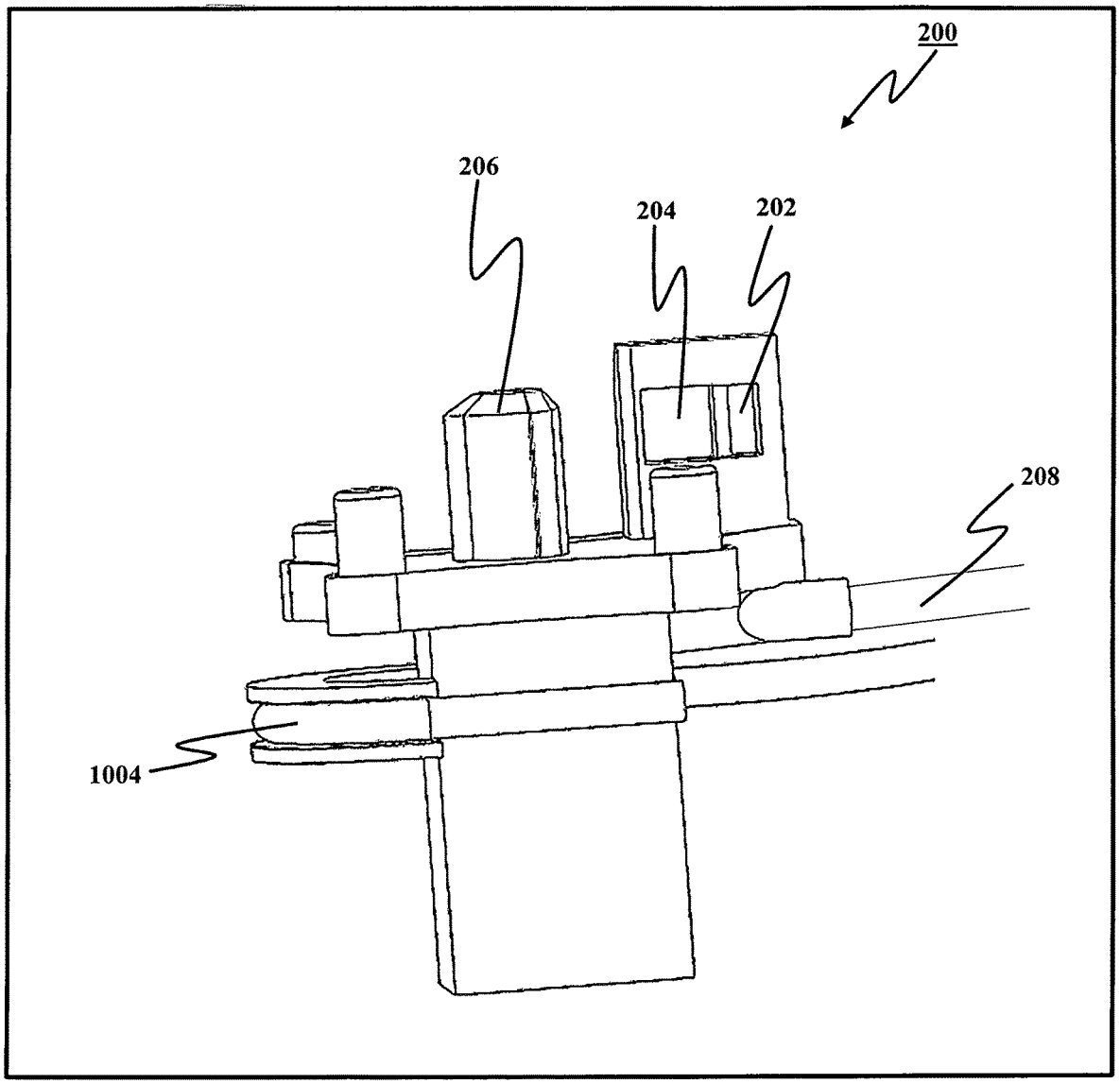

FIGS. 3A & 3B depicts exemplary views of the second housing 200 in accordance with an embodiment of the invention. The second housing 200 may be connected to the body frame of the head mounting device 1004 as shown in the figures. The second housing 200 is connected to the head mounting device 1004 such that, the position of the second housing 200 with respect to the subject 1002 may be adjusted and then locked. A lead cable 208 connects the controller 1006 to the second housing 200. Alternatively, the controller 1006 may be attached directly to the second housing 200 or may be positioned inside the second housing 200 to achieve a compact design depending on the use case.

The second housing 200 includes an actuator, a photoresistor and a Light Emitting Diode (LED), which are operably connected to the controller 1006 through the lead cable 208. The actuator (not shown in the figures) is positioned inside the second housing 200. The photoresistor is positioned inside a compartment 204, and the LED is positioned inside a compartment 202. In an embodiment, the compartments 202 and 204 are positioned such that at least a part of the reflected light from the LED in compartment 202 is captured by the photoresistor in the compartment 204. In an embodiment, the LED and the photoresistor may be replaced by an infrared diode and infrared receiver in the compartment 202 and compartment 204, respectively.

Figure 3C:
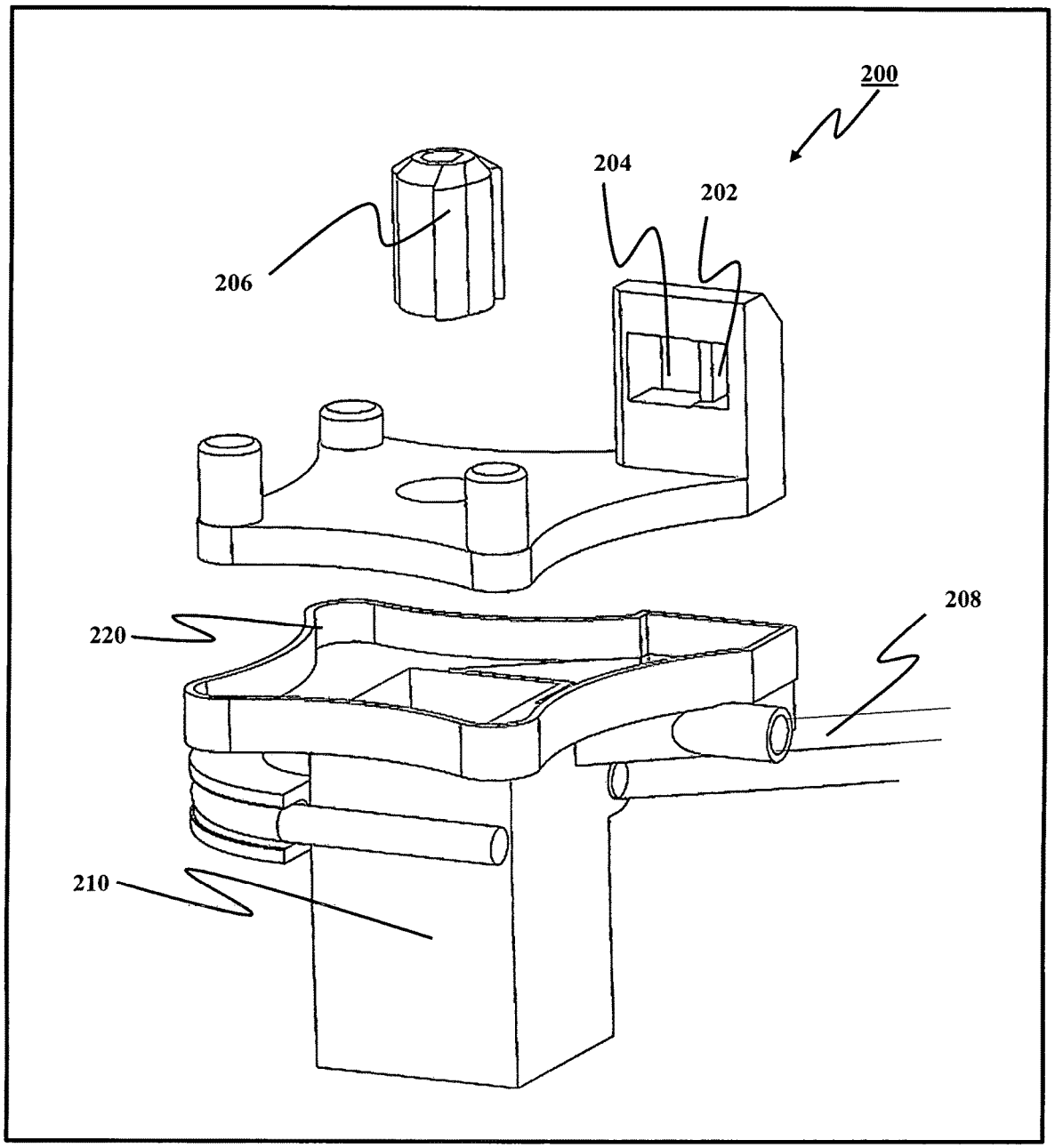
FIG. 3C illustrates an exploded view of the second housing 200 in accordance with an embodiment of the invention.

FIG. 3C illustrates an exploded view of the second housing 200 in accordance with an embodiment of the invention. The second housing 200 is formed by connecting the first section 210 and the second section 220. The first section 210 houses the actuator and the second section 220 houses the compartment 202 and the compartment 204 for holding the LED and the photoresistor, respectively. An extension shaft 206 is connected to the shaft of the actuator in the first section 210. The second section 220 (also referred to as "top surface" of the second housing 200) as depicted in the figures may include one or more protrusion to receive the first housing 100.

Figure 4A:
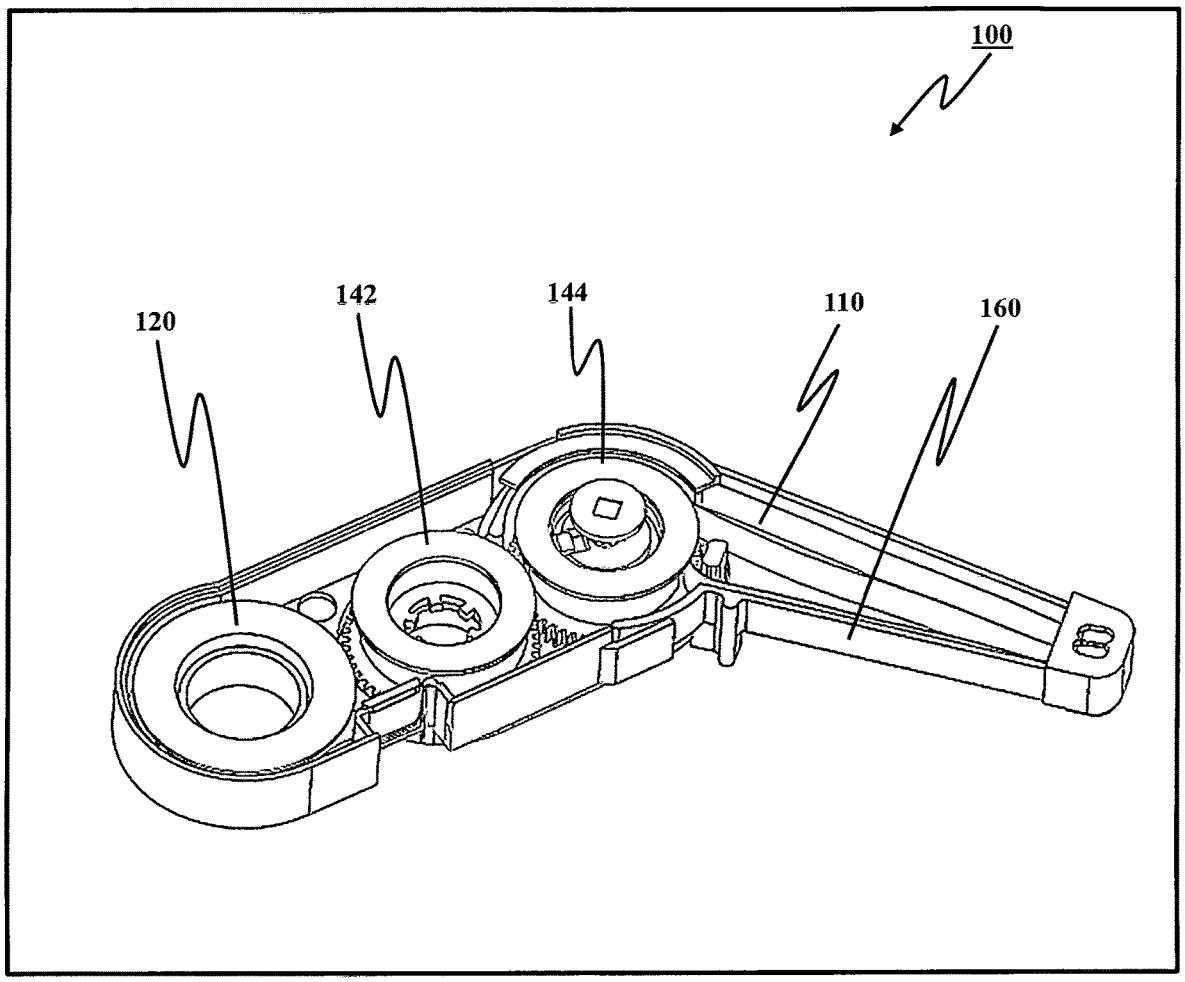
FIG. 4A depicts an exemplary view of the first housing 100 without a lid 180, in accordance with an embodiment of the invention.
Figure 4B:
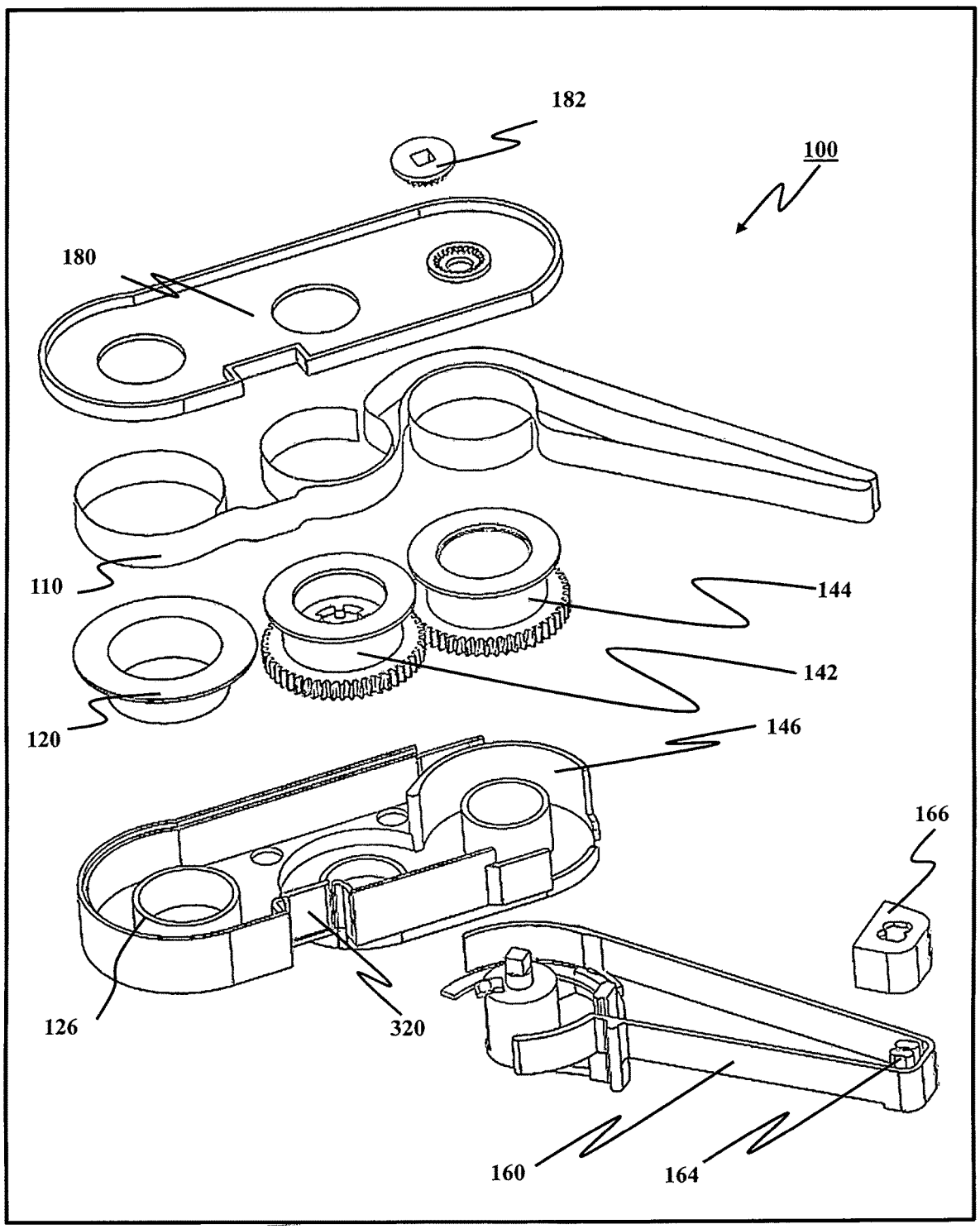
FIGS. 4B & 4C depicts an exemplary exploded view of the first housing 100, in accordance with an embodiment of the invention.
Figure 4C:
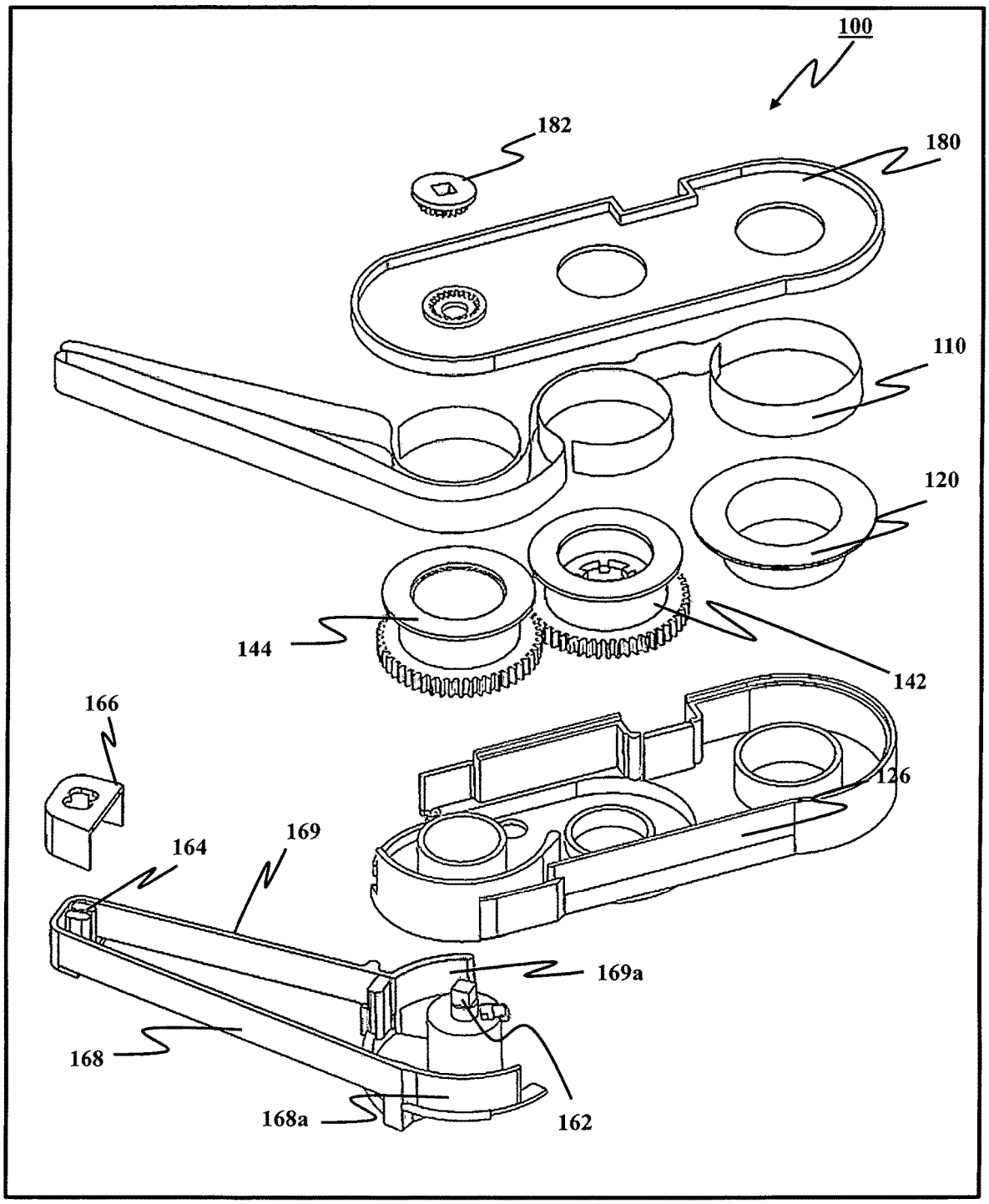

FIG. 4A depicts an exemplary view of the first housing 100 without a lid 180, in accordance with an embodiment of the invention. The first housing 100 includes a cartridge spool 120, a drive mechanism, a nose piece 160, and the lid 180. The drive mechanism includes a first spool gear 142 and a second spool gear 144. FIGS. 4B & 4C depicts an exemplary exploded view of the first housing 100, in accordance with an embodiment of the invention. The cartridge spool 120 includes a tape cartridge 110.

Figure 5A:
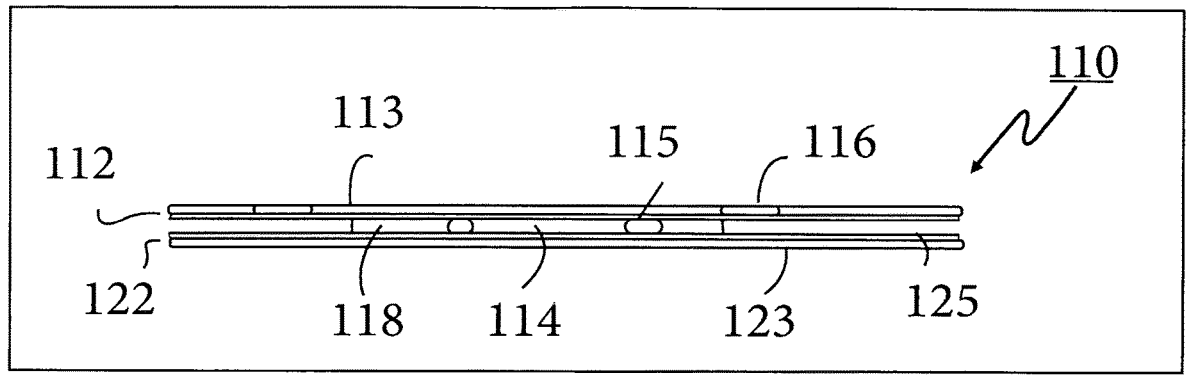
FIG. 5A illustrates a side view of the tape cartridge 110, in accordance with an embodiment of the invention.
Figure 5B:
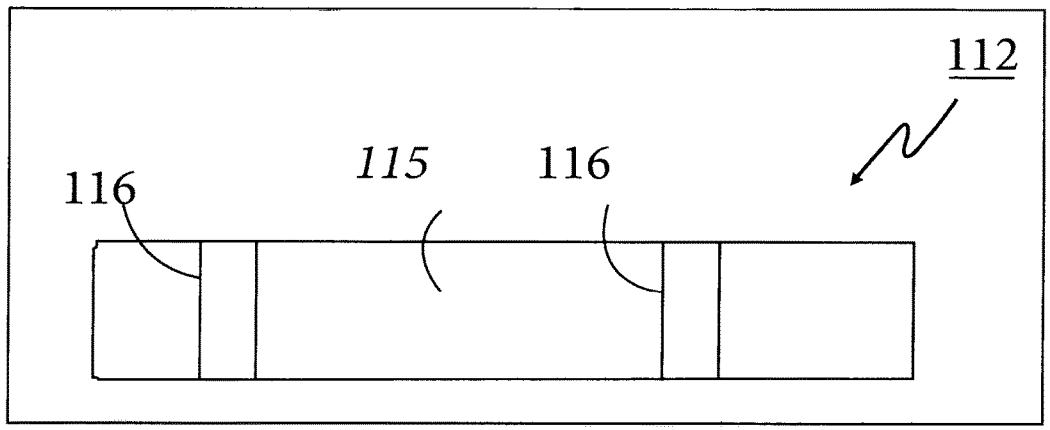
FIG. 5B illustrates the outer surface 113 of the first film 112 of the tape cartridge 110, in accordance with an embodiment of the invention.

FIG. 5A illustrates a side view of the tape cartridge 110, in accordance with an embodiment of the invention. The tape cartridge 110 include a first film 112 and second film 122. The first film 112 has an outer surface 113 and an inner surface 115. The outer surface 113 may be blue in color, and the inner surface 115 may be silver in color, as depicted in the FIGS. 5B & 5C. As depicted in FIG. 5B, the first film may include one or more black strip 116 on its outer surface 113.

Figure 5C:
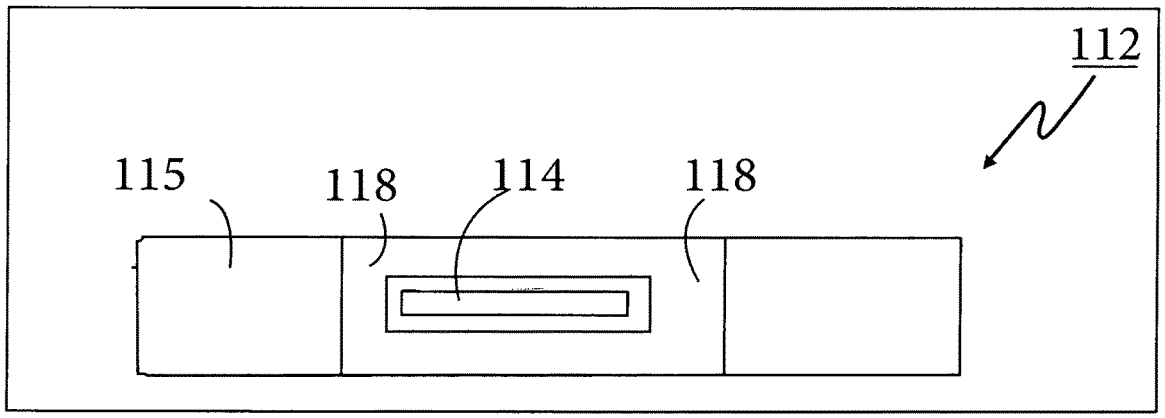
FIG. 5C illustrates the inner surface 115 of the first film 112 of the tape cartridge 110, in accordance with an embodiment of the invention.

FIG. 5C illustrates the inner surface 115 of the first film 112 of the tape cartridge 110, in accordance with an embodiment of the invention. The inner surface 115 of the first film 112 may be silver in color, and a scent zone 114 is attached to the inner surface 115 using an adhesive 118. In an embodiment the position of the scent zone 114 on the inner surface 115 may be in between two successive black strip 116 on the outer surface 113 of the first film 112, as depicted in FIG. 5A. In an exemplary embodiment, the adhesive 118 may be rectangular in shape and the scent zone 114 is positioned on the rectangular adhesive 118.

The second film 122 has an outer surface 123 and an inner surface 125. The outer surface 123 may be blue in color, and the inner surface 125 may be silver in color. The inner surface 125 of the second film 122 is pressed directly to the adhesive 118 on the first film, such that the scent zone 114 is removably sealed (also referred to as "sealed") or sandwiched between the first film 112 and the second film 122. In an embodiment, the scent zone may be removably attached using a pressure sensitive adhesive. In an embodiment, the scent zone 114 may include scent in the form of, but not limited to, one or more or a power, a wax, and a gel, among other forms.

Referring to FIG. 4B, the dive mechanism may include a mechanism to advance the tape cartridge 110 from the cartridge spool and expose the scent in the scent zone 114 to the subject's nostrils. In an embodiment, the drive mechanism includes the first spool gear 142, and the second spool gear 144. Further the drive mechanism may collect the first film 112 and second film 122 of the tape cartridge 110, which may be split at the nose piece 160.

Figure 4D:
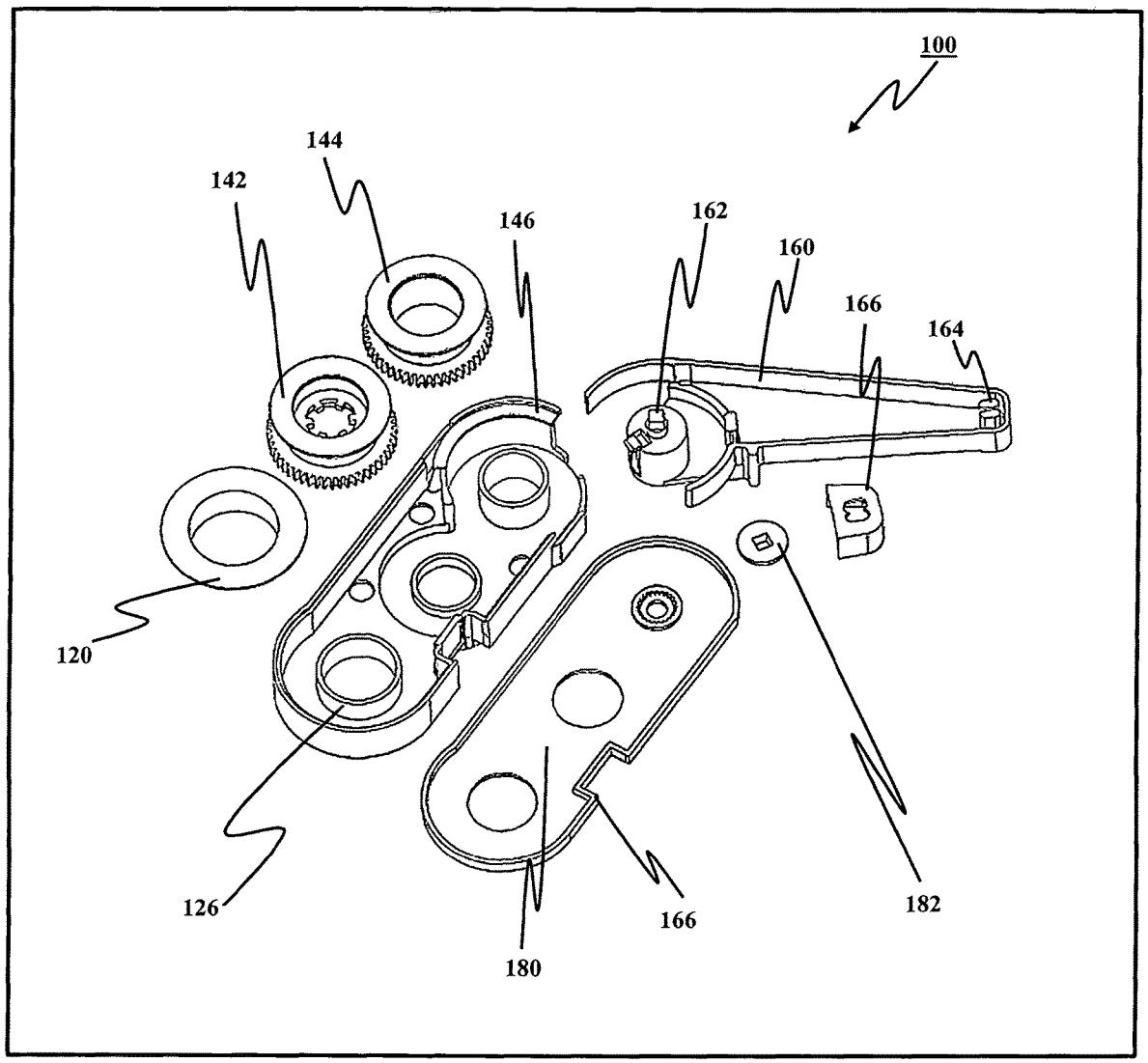
FIGS. 4D & 4E depicts an exemplary view of the first housing 100 without tape cartridge 110, in accordance with an embodiment of the invention.
Figure 4E:
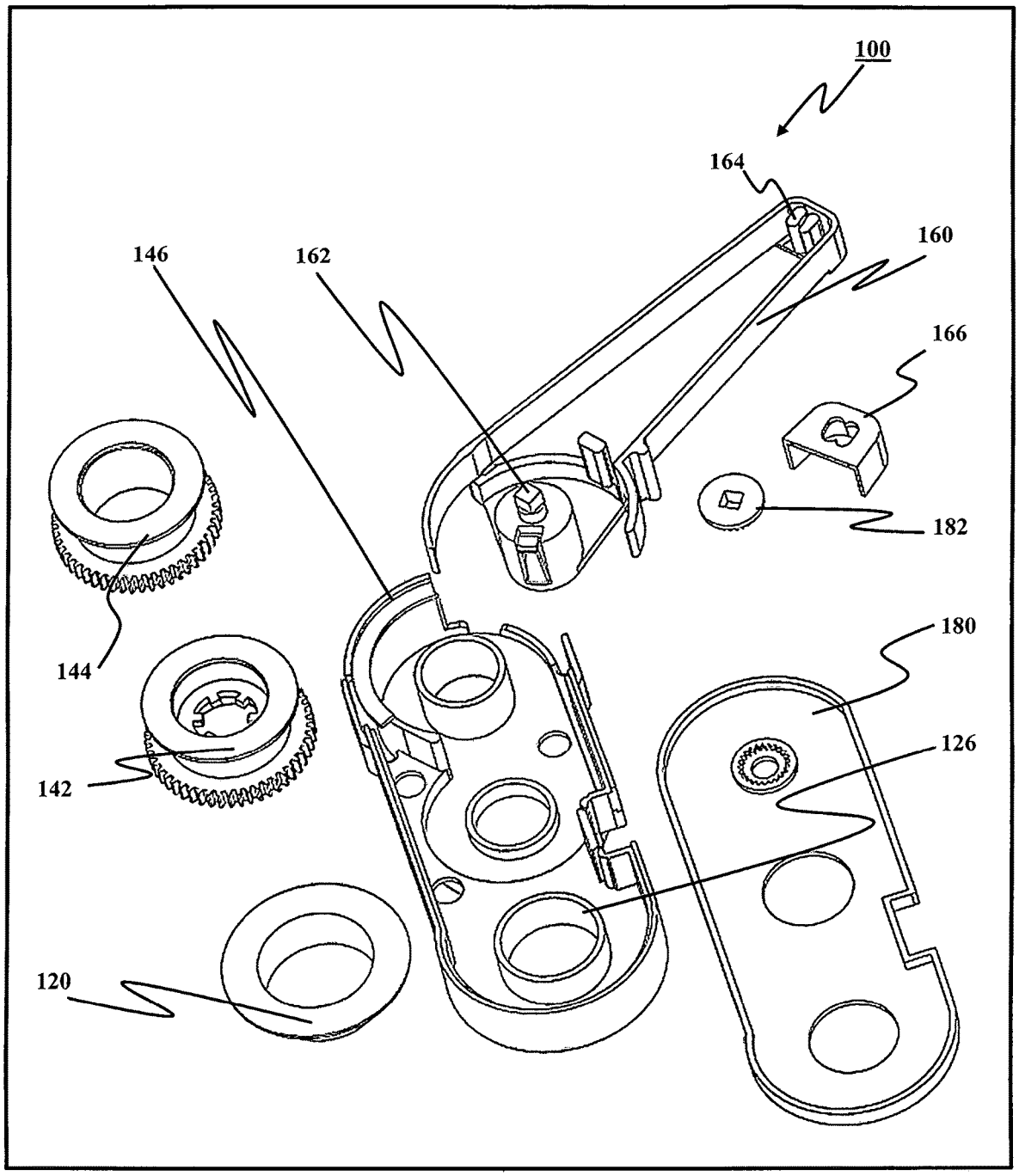

FIGS. 4D & 4E illustrate another view of first housing 100 without the tape cartridge 110, in accordance with an embodiment of the invention. The drive mechanism may include the first spool gear 142 and the second spool gear 144, which are positioned such that, the actuator in the first section 210 actuate the first spool gear 142, through an extension shaft 206. Further, the position of the second spool gear 144 is such that, the first spool gear 142 drives the second spool gear 144, as depicted in the FIG. 4F.

Figure 7:
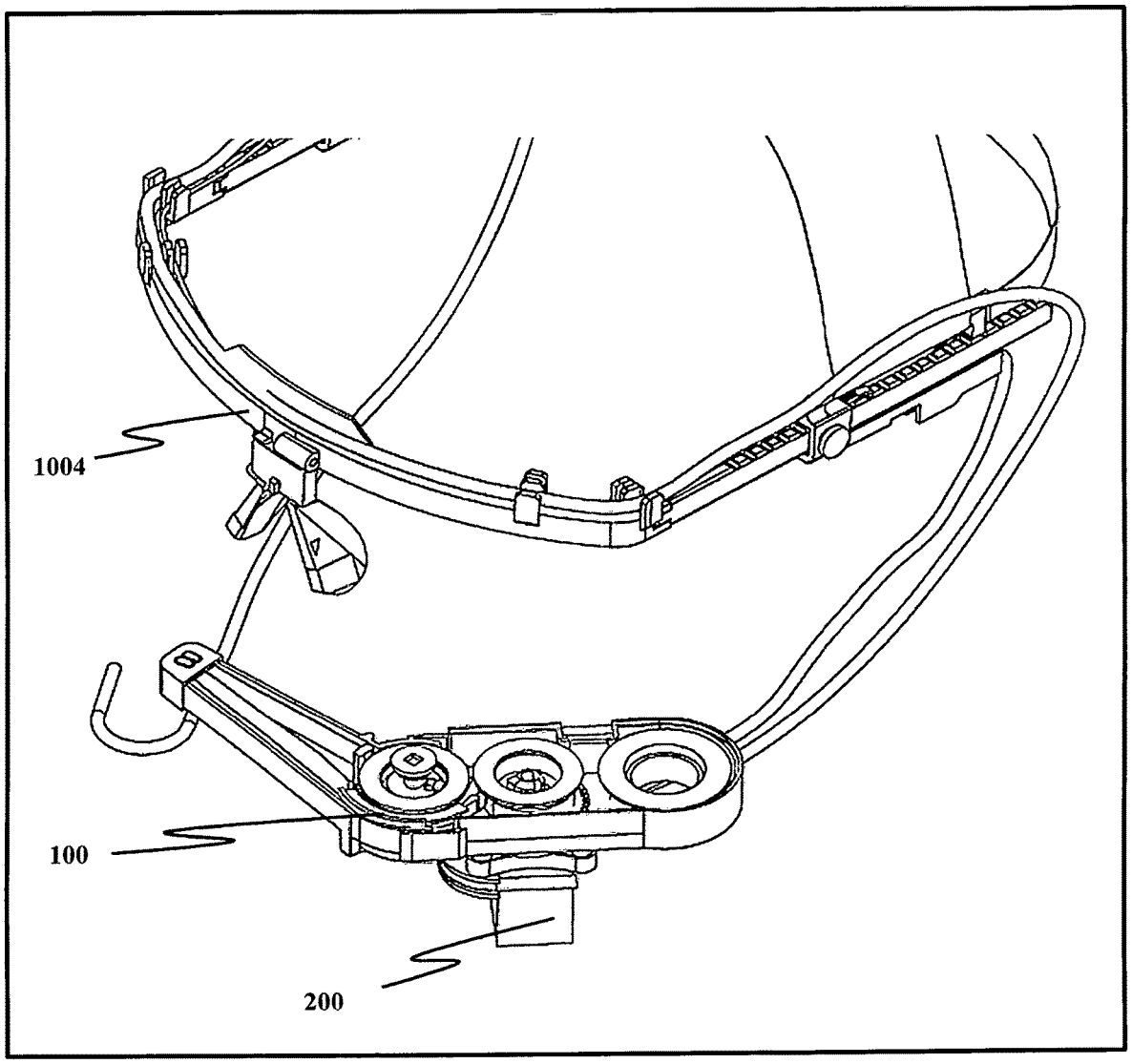
FIG. 7 depicts an exemplary view of the scent dispenser device 1000 attached to a head mounting device 1004, without a lid 180, in accordance with an embodiment of the invention.

Referring to the FIGS. 4B-4E, the nose piece 160 of the first housing 100 includes a pair of splitters 164, a pivot button male 162, a first wall 168 terminating at a first shield 168a and a second wall 169 terminating at a second shield 169a, as depicted in FIG. 4C. The nose piece 160 splits the tape cartridge 110 at the pair of splitters 164 and exposes the scent from the scent zone 114 to the nostrils of the subject 1002, as depicted in FIGS. 1 & 7. The first shield 168a and the second shield 169a may protect the subject 1002 from the advancing tape cartridge 110. The pair of splitters 164 are covered by a splitter cover 166 to prevent slipping of the tape cartridge 110 of the nose piece 160.

Figure 4F:
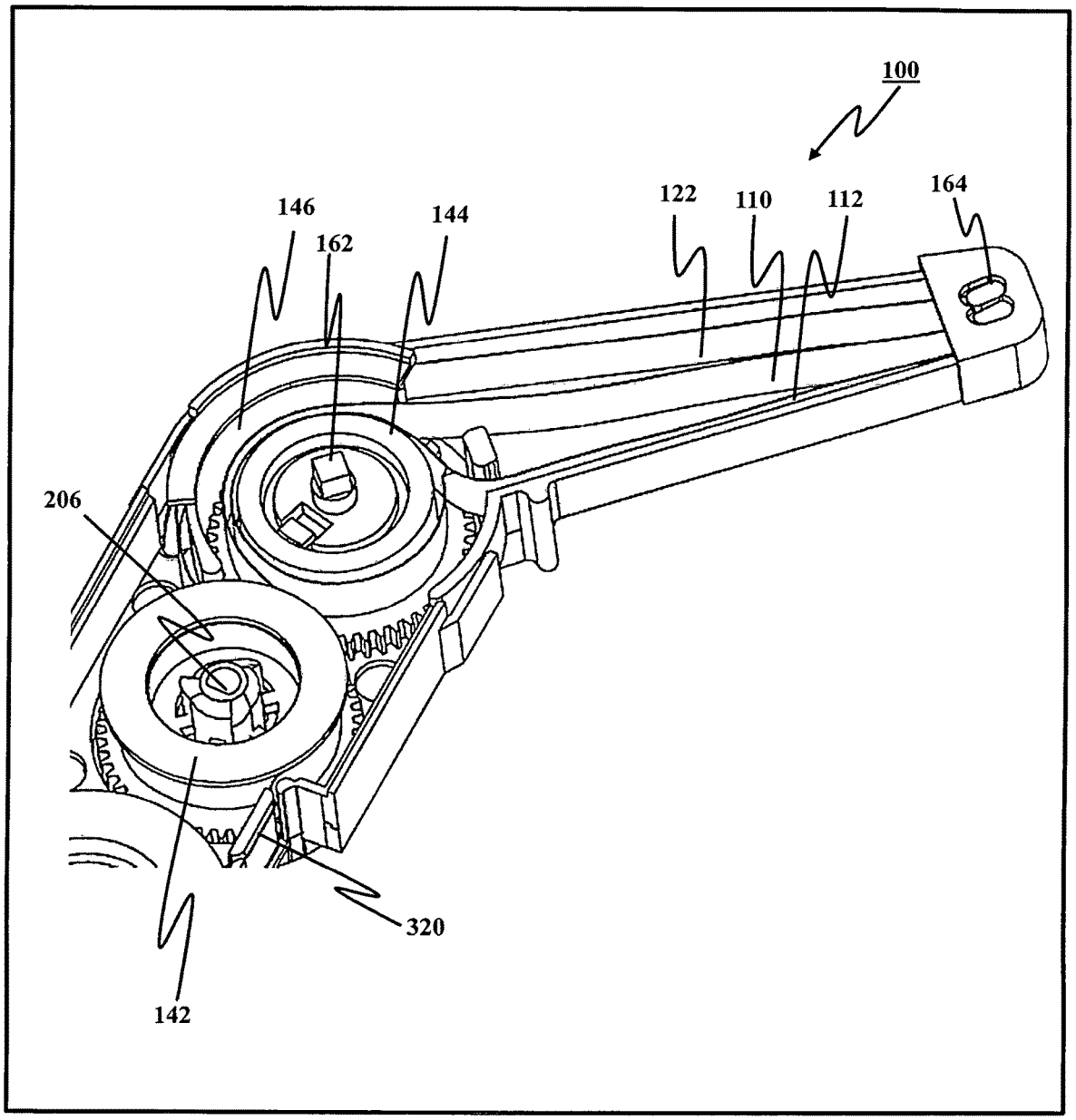
FIG. 4F depicts an exemplary view of the drive mechanism of the first housing 100, in accordance with an embodiment of the invention.
Figure 6A:
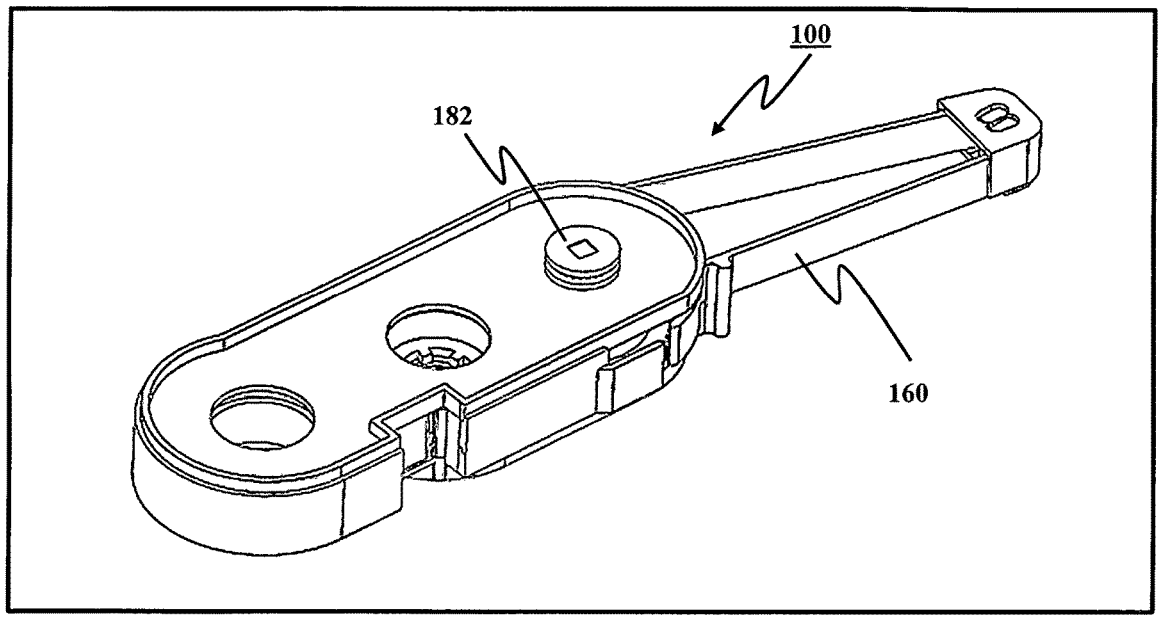
FIGS. 6A & 6B illustrates the nose piece 160 pivoting about the second spool gear 144, in accordance with an embodiment of the invention.
Figure 6B:
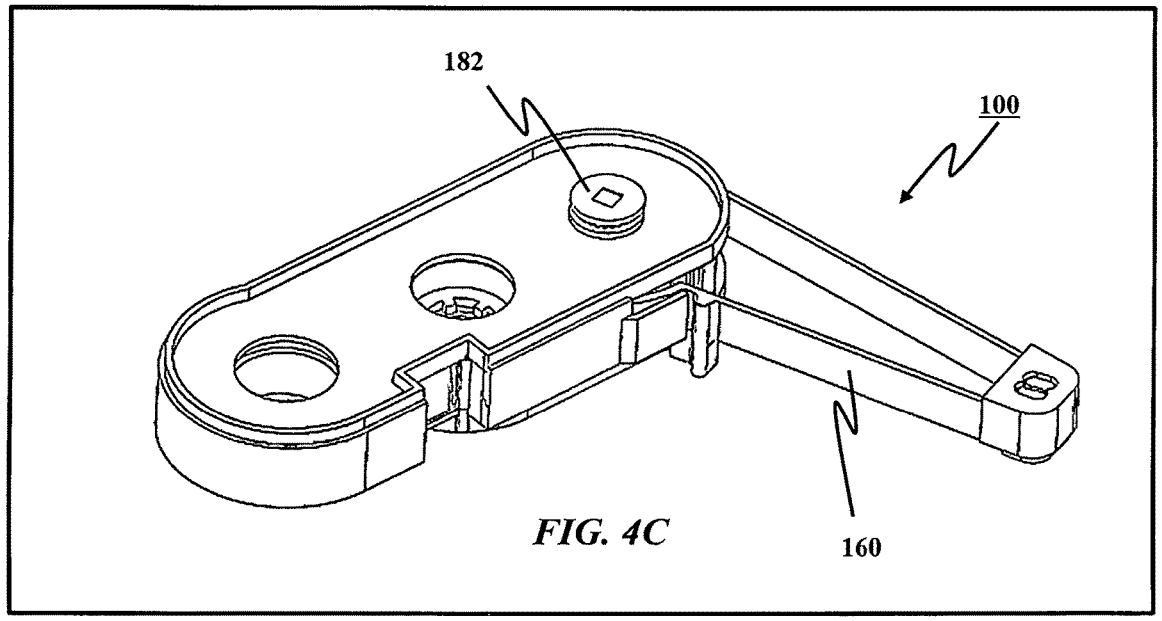

The pivot button male 162 is received by the hollow second spool gear 144, as depicted in the FIG. 4F. The pivot button male 162 extents through the second spool gear 144 till the top of the lid 180. The pivot button male 162 may be connected to the pivot button 182, as shown in FIGS. 6A & 6B to prevent the nose piece 160 from pivoting when the drive mechanism is in operation. The lid 180 may be press fitted to the first housing to secure the position of all the internal parts of the first housing 100.

FIGS. 6A & 6B illustrates the nose piece 160 pivoting about the second spool gear 144, in accordance with an embodiment of the invention. The nose piece 160 may be pivoted about the second spool gear 144 through the pivot button male 162 secured inside the hollow second spool gear 144. The subject 1002 may adjust the position of the nose piece 160 as per the subject's 1002 comfort to smell the scent of the exposed scent zone 114. The scent zone 114 is exposed at the nose piece 160 close to the nostrils of the subject 1002. The position of the nose piece 160 with respect to first housing 100 in FIG. 6A is different from the position of the nose piece 160 with respect to first housing 100 in FIG. 6B.

Movement of the Tape Cartridge 110 within the First Housing 100

Figure 4G:
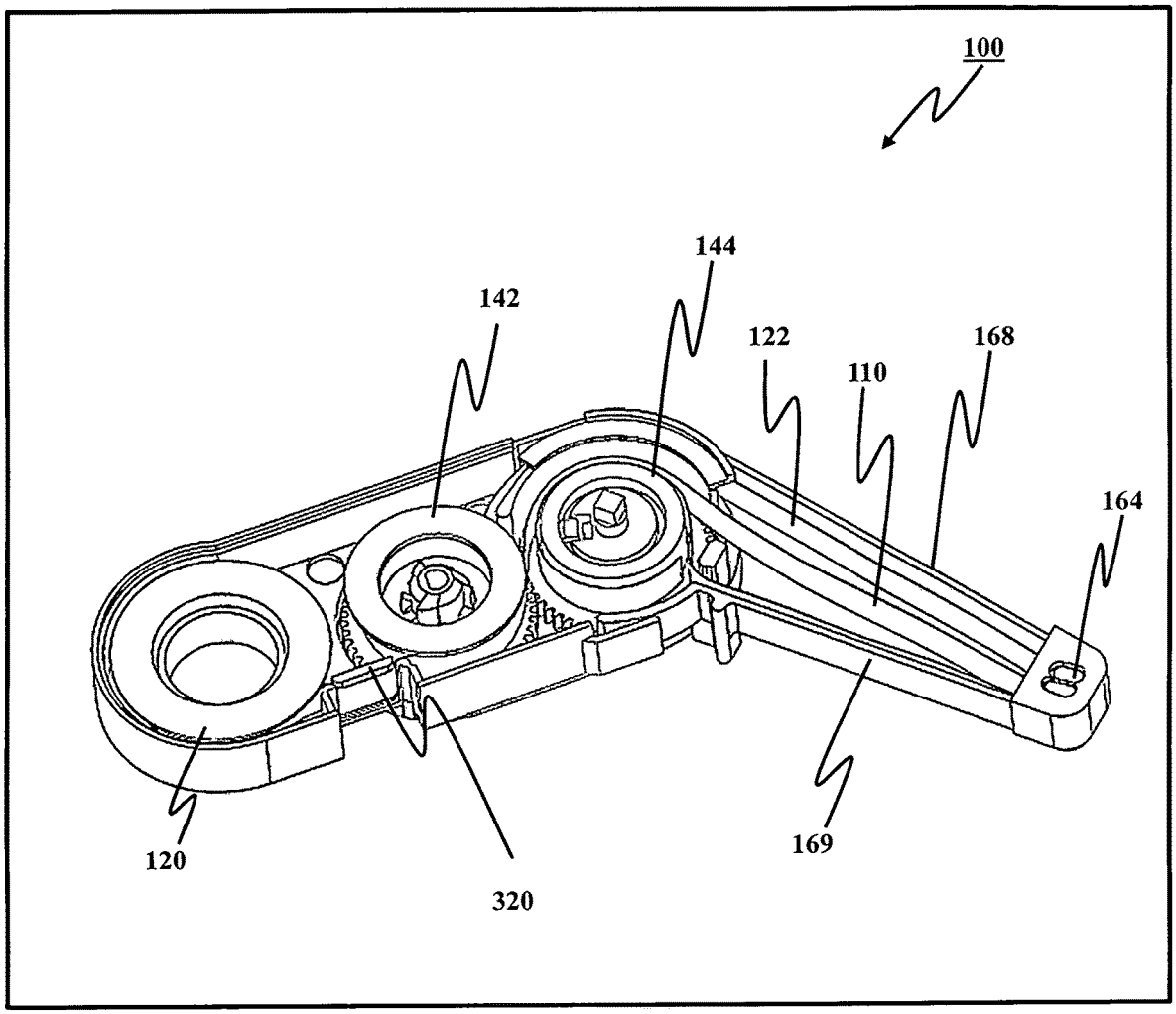
FIG. 4G depicts another exemplary view of the first housing 100 without a lid 180, in accordance with an embodiment of the invention.

Referring to the FIGS. 4F & 4G, the tape cartridge 110 is secured in the first housing 100. In an exemplary embodiment, the tape cartridge 110 may be spooled to the cartridge spool 120, whose position is held by a cylindrical protrusion 126 within the first housing, as depicted in the figures. Alternatively, the tape cartridge 110 may be folded in a zig-zag pattern within the first housing and before the drive mechanism. Alternatively, other configurations like circular folding may also be implemented and are within the scope of this invention.

Further, the tape cartridge 110 from the cartridge spool 120 passes through a slit bridge 320 (also refer to FIG. 4B). The passage of the tape cartridge 110 through the slit bridge 320 is exposed from the first housing (refer to FIG. 4G). The slit bridge creates tension on the tape cartridge 110 and prevents the scent cartridge from slipping more than required into the drive mechanism. The slit bridge 320 may also prevent the tape cartridge 110 from folding. Further, the tape cartridge 110 is directed towards the drive mechanism.

Further, as depicted in the FIGS. 4F & 4G, the tape cartridge 110 in the drive mechanism passes diagonally between the first spool gear 142 and the second spool gear 144 to the pair of splitters 164 of the nose piece 160. The pair of splitters 164 splits the tape cartridge 110 in to first film 112 and the second film 122, thereby exposing the scent in the sealed scent zone 114 of the tape cartridge 110.

Further, the second film 122 is channeled for spooling through a return wall 146 (refer to FIG. 4F) at the first spool gear 142. The return wall 146 facilitate smooth flow of the second film 122 from the pair of splitters 164 to the first spool gear 142. The return wall 146 may prevent jamming of the striped second film 122 inside the drive mechanism. The passage of the second film 122 from the pair of splitters to the first spool gear 142 is protected by the first wall 168 and the first shield 168a. The second film 122 is guided to the first spool gear 142 through the gap between the return wall and the first shield 168a. One end of the second film 122 is connected to the first spool gear 142 through the return wall 146, before the scent dispenser device is in operation. The one end of the second film 122 may be connected using an adhesive to the first spool gear 142.

Further, the first film 112 is channeled for spooling at the second spool gear 144. The passage of the first film 112 from the pair of splitters to the second spool gear 144 is protected by the second wall 169 and the second shield 169a. One end of the first film 112 is connected to the second spool gear 144 before the scent dispenser device is in operation. The one end of the first film 112 may be connected using an adhesive to the second spool gear 144.

Operation of the Scent Dispenser Device 1000

Figure 4H:
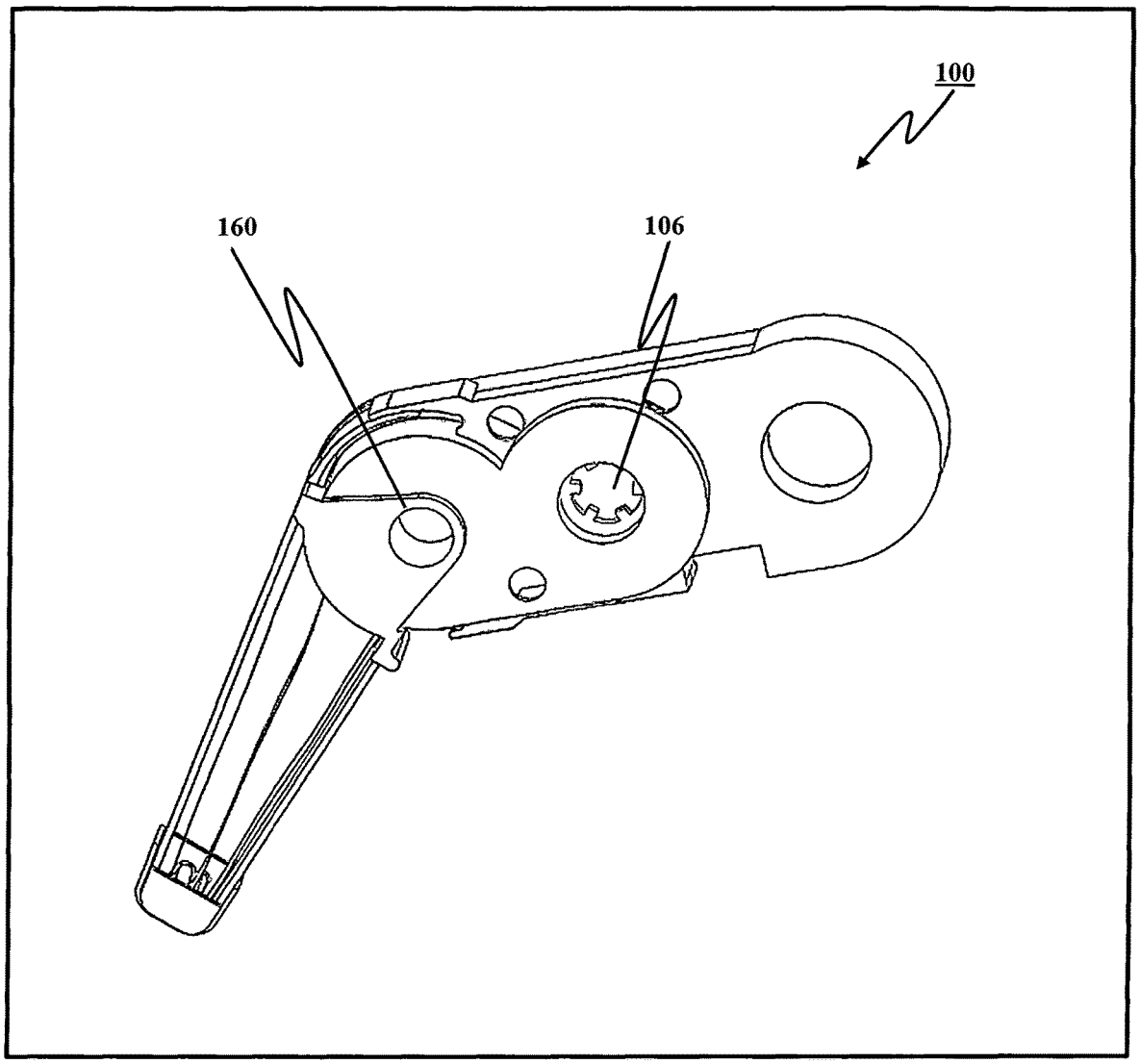
FIG. 4H depicts an exemplary bottom view of the first housing 100, in accordance with an embodiment of the invention.

The extension shaft 206 is connected to the first spool gear 142 through an aperture 106 (refer to FIG. 4H) at the bottom surface of the first housing 100. In an embodiment, when the scent dispenser device 1000 is turned on (also referred to as "in operation"), the actuator actuates the first spool gear 142 through the extension shaft 206. Further, the first spool gear 142 drives the second spool gear 144 in opposite direction to the first spool gear. One end of the second film 122 is connected to the first spool gear 142, and one end of the first film 112 is connected to the second spool gear 144. Subsequently, while the actuator is turned on, the second film 122 and the first film 112 are spooled at the first spool gear 142 and the second spool gear 144, respectively. Simultaneously, the scent from the scent zone 114 is exposed, by the pair of splitters 164, near the nostrils of the subject for the subject 1002 to smell.

In an embodiment, the first housing 100 and second housing 200 are detachably coupled through one or more recess and protrusion (refer to FIGS. 2A-2C & 4H), such that the slit bridge 320 is positioned against the compartment 204 and compartment 202 of the second housing 200, as depicted in FIGS. 2A-2C, & 4B.

In the instance the scent dispenser device 1000 is set to operation by the controller 1006, the LED in the compartment 202 is turned on and illuminates light so that the photoresistor in compartment 204 captures the reflection value. The light of the LED is reflected from the outer surface 113 of the first film 112. The reflection is measured by the photoresistor in the compartment 204. When a change in the measured value of reflection is identified by the controller 1006, the operation of the actuator in the second housing 200 is altered by the controller 1006.

For example, the outer surface 113 of the first film 112 is blue in color with black strip 116 there between along the length of the tape cartridge 110. In general, the light color matching the color of the reflecting surface provides a value closest to "white". A blue color outer surface is a good reflector of light from the LED light emitting blue light, as compared to black color. Hence, when the actuator is in operation the value of reflection measured by the controller 1006 through the photoresistor in the compartment 204 is relatively constant. Further, when the black strip 116 appears against the LED light the reflection measured by the controller 1006 through the photoresistor in the compartment 204 changes. The controller 1006 upon detecting this change in the measured reflection value may modify the operation of the actuator.

In an embodiment, the controller 1006 may turn off the actuator in the second housing 200 upon detecting the black strip 116 against the LED light in the compartment 202. Further, upon receiving an external signal, the controller 1006 may again turn on the actuator and continue its operation until a change in the measured reflection value is detected. In an embodiment, the external signal timing may be preprogramed or stored based on the motion picture being viewed by the subject 1002.

In an exemplary embodiment, the scent dispenser device 1000 may be fully assembled and ready to use for a subject 1002. Further, the subject 1002 may connect the scent dispenser device 1000 to a controller of a head mounting device 1004. Thereafter, secure the scent dispenser device 1000 to the head mounting device 1004 as depicted in the FIGS. 1 & 7. Further, the subject 1002 may adjust the nose piece 160 position by holding the second housing 200 or the first housing 100, in order to position the nose piece 160 below and close to the nostrils of the subject 1002. Further press the pivot button 182 to prevent the further movement of the nose piece 160. Finally, once the tape cartridge is finished, the subject 1002 may lift up the first housing 100 in order to detach it from the second housing 200. Thus, the first housing 100 may be disposable upon single use. However, a new first housing 100 may be detachably connected to the same second housing 200 for subsequent use, which makes the second housing reusable and the first housing is disposed upon single use.

In an embodiment, the one or more scent zone 114 may be of a single or multiple fragrance. In an alternative embodiment, the tape cartridge 110 may contain elevated pockets. In another alternative embodiment, the tape cartridge 110 may have a 3 layer of film, where one-layer peels back with a piece of the middle layer.

The present invention overcomes the drawbacks of the conventional solutions, by providing a scent dispenser device to enhance the user experience of viewer. The present invention as discussed in this document with respect to different embodiments may be advantageous at least in enhancing the user experience of a viewer of motion pictures such as, but not limited to, movies, video games and other videos. This is enabled by providing a compact, inexpensive and personalized headset attachment that dispenses a customized scent from one or more scent zone based on footage the viewer is watching and at appropriate time. This invention is further advantageous in providing a cartridge with scent zones that may expose the scent to the nostrils of a user at an appropriate time based on the motion picture content viewed by the subject. The invention is further advantageous in providing a scent dispenser device that is adjustable and does not interfere with other sensory devices mounted on the same head mounting device, such as flavor or taste, audio, visual, and feel. Additional advantages not listed may be understood by a person skilled in the art in light of the embodiments disclosed above.

Although embodiments have been described with reference to specific example embodiments, it may be evident that various modifications and changes may be made to these embodiments without departing from the broader spirit and scope of the scent dispenser device. Accordingly, the specification and drawings are to be regarded in an illustrative rather than a restrictive sense.

Many alterations and modifications of the present invention may no doubt become apparent to a person of ordinary skill in the art after having read the foregoing description. It is to be understood that the phraseology or terminology employed herein is for the purpose of description and not of limitation. It is to be understood that the description above contains many specifications; these should not be construed as limiting the scope of the invention but as merely providing illustrations of some of the personally preferred embodiments of this invention. Thus, the scope of the invention should be determined by the appended claims and their legal equivalents.

What is claimed is:

1. A scent dispenser device configured to be used by a subject watching a motion picture, the scent dispenser device comprising:
    a first housing positioned close to the nostrils of the subject, wherein the first housing comprises:
        a tape cartridge, which includes one or more scent zone; wherein the tape cartridge further comprises a first film and a second film; and wherein the one or more scent zone is sandwiched between the first film and the second film, such that the one or more scent zone is sealed, and wherein the outer surface of the first film includes one or more black strip;
        a drive mechanism to advance the tape cartridge inside the first housing; and
        a nose piece configured to split the tape cartridge into the first film and the second film, such that the scent from the one or more scent zone is exposed to the nostrils of the subject by the nose piece when the drive mechanism is in operation.

2. The scent dispenser device according to claim 1, wherein the nose piece is movably attached to the drive mechanism of the first housing, such that the position of the nose piece with respect to the first housing is adjustable.

3. A head mounting device comprising:
    a body frame to secure the head mounting device to a subject's head;
    a scent dispenser device attached to the body frame with an armature, and configured to be used by the subject watching a motion picture, the scent dispenser device comprises:
        a first housing, positioned close to the nostrils of the subject, wherein the first housing comprises:
            a tape cartridge, which includes one or more scent zone; and a drive mechanism to advance the tape cartridge inside the first housing, wherein the drive mechanism comprises a first spool gear and a second spool gear positioned such that the first spool gear drives the second spool gear in case the drive mechanism is in operation, and an actuator operably coupled to the first spool gear to actuate the drive mechanism,
            wherein the scent of the one or more scent zone is exposed to the nostrils of the subject, in case the drive mechanism is in operation;
    a controller communicably connected to the scent dispenser device, wherein the controller is configured to operate the drive mechanism;
    a second housing, wherein the actuator is secured in the second housing; and
    wherein the second housing is detachably connected to the first housing, such that the actuator drives the first spool gear in the first housing, and wherein the second housing further comprises a photoresistor and a Light Emitting Diode (LED); and wherein the photoresistor and the LED are positioned against the tape cartridge when the first housing is connected to the second housing, such that the light emitted by the LED is reflected of the tape cartridge and the reflected light is received by the photoresistor.

4. The head mounting device according to claim 3, wherein the controller is configured to detect the change in a reflection measurement of the photoresistor; and modify the operation of the actuator.

5. The head mounting device according to claim 3, further comprising:
    a cartridge spool, wherein the tape cartridge is spooled to the cartridge spool; and
    a cylindrical protrusion, within the first housing, configured to secure the position of the cartridge spool.

6. A scent dispenser device configured to be used by a subject watching a motion picture, the scent dispenser device comprising:

a first housing, positioned close to the nostrils of the subject, wherein the first housing comprises:
  a tape cartridge, wherein the tape cartridge comprises:
    a first film;
    a second film; and
    one or more scent zone sandwiched between the first film and the second film;
  a nose piece movably attached to the first housing; and wherein the nose piece splits the first film and the second film of the tape cartridge to expose the scent from the one or more scent zone to the nostrils of the subject; and
  a drive mechanism, wherein the drive mechanism comprises a first spool gear and a second spool gear positioned, such that the first spool gear drives the second spool gear to advance the tape cartridge inside the first housing, and wherein the scent from the one or more scent zone is exposed by the nose piece in case the drive mechanism is in operation.

* * * * *